United States Patent [19]

Morgan et al.

[11] 4,086,302
[45] Apr. 25, 1978

[54] PHOSPHOROAMIDATES

[75] Inventors: Albert W. Morgan, Collinsville, Ill.; Ignatius Schumacher; William Vanderlinde, both of St. Louis, Mo.

[73] Assignee: Monsanto Company, St. Louis, Mo.

[21] Appl. No.: 727,913

[22] Filed: Sep. 29, 1976

Related U.S. Application Data

[60] Continuation-in-part of Ser. No. 599,569, Jul. 28, 1975, abandoned, which is a division of Ser. No. 459,257, Apr. 8, 1974, abandoned, which is a continuation-in-part of Ser. No. 276,810, Jul. 31, 1972, abandoned.

[51] Int. Cl.² ............... C07F 9/24; C07F 9/65
[52] U.S. Cl. .............................. 260/926; 260/2 P; 260/268 K; 260/293.64; 260/307 F; 260/928; 260/930; 260/940; 260/941; 260/950; 260/951; 260/954; 260/955; 260/959; 260/960; 536/117; 544/57; 544/84; 544/157
[58] Field of Search ................. 260/926; 536/117

[56] References Cited

U.S. PATENT DOCUMENTS

| | | | |
|---|---|---|---|
| 2,870,189 | 1/1959 | Blair et al. | 260/926 |
| 2,944,075 | 7/1960 | Debo | 260/926 X |
| 2,950,308 | 8/1960 | Dunbar | 260/926 |

Primary Examiner—Richard L. Raymond
Attorney, Agent, or Firm—George R. Beck; Robert E. Wexler; Edward P. Grattan

[57] ABSTRACT

Compounds of the formulas

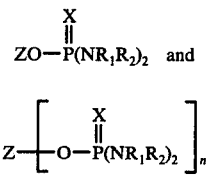

wherein:
X represents oxygen or sulfur;
Z represents the residue of a hydroxyl-containing moiety;
$R_1$ and $R_2$ in formula (1) may be the same or different and individually represent alkyl, cycloalkyl or aryl and, together with the common nitrogen atom, represent a 5 or 6 member ring containing oxygen, sulfur or nitrogen or combination thereof;
$NR_1R_2$ in formula (2) represents a 5 or 6 member ring containing oxygen, sulfur or nitrogen or combination thereof;
n represents an integer having a value of 2 or greater and is equal to the number of hydroxyl groups on the orginal hydroxyl-containing moiety, the residue of which is now represented by Z.

are prepared by reacting a phosphorohalidate with an amine in an organic solvent containing aqueous alkali metal or ammonium hydroxide.

The compounds are useful as flame retardants for natural and synthetic materials.

2 Claims, No Drawings

PHOSPHOROAMIDATES

CROSS-REFERENCES TO RELATED APPLICATIONS

This application is a continuation-in-part of copending application Ser. No. 599,569, filed July 28, 1975, now abandoned, which was a divisional of application Ser. No. 459,257, filed Apr. 8, 1974, now abandoned which was a continuation-in-part of application Ser. No. 276,810 filed July 31, 1972, now abandoned.

BACKGROUND OF THE INVENTION

This invention relates to (a) a novel process for preparing phosphoroamidates, (b) novel flame retardant polymer compositions containing certain known phosphoroamidates, (c) novel phosphoroamidates and (d) novel flame retardant polymer compositions containing novel phosphoroamidates.

(a) Process

In the past, one method of preparing phosphoroamidates has been carried out by reacting a corresponding phosphorohalidate with an excess of an appropriate amine in an organic diluent. This method is disadvantageous since salts are formed during the reaction which precipite from the organic solution and must be separated and since the only means of scavenging hydrogen chloride formed during the reaction is by the use of excess amine which is quite expensive.

It was also known, of course, that aqueous caustic is a hydrogen chloride scavenger but that knowledge was not believed adaptable to the preparation of phosphoroamidates since it appeared obvious that aqueous caustic would hydrolyze the intermediate phosphorohalidate to phosphoric acid.

(b) Known Phosphoroamidates

The following patents disclose phosphoroamidates prepared from simple aliphatic and aromatic alcohols, phosphorus oxyhalide or thiohalide and an amine:

U.S. Pat. No. 2,385,713   U.S. Pat. No. 3,531,550
U.S. Pat. No. 2,912,451   U.S. Pat. No. 3,584,085
U.S. Pat. No. 3,328,494

U.S. Pat. No. 2,385,713 discloses compounds of the formula $(Phenyl-O)_m P(O)(NX_2)_n$ wherein $X = H$ or hydrocarbon and $m + n = 3$. The compounds are esters of amidophosphoric acids with substituted phenols and have utility as germicides and bactericides. With regard to the present invention, the patent indicates no distinction between the use of primary and secondary amines, contains an enabling disclosure directed only to "diamidophosphates" and, while disclosing certain compounds within the scope of formula (1) of this invention, does not teach the use of phosphorodiamidates as flame retardants.

U.S. Pat. No. 2,912,451 discloses acyclic tetramethylphosphorodiamidates having utility as weed killers. With regard to the present invention, the patent discloses amidation only with dimethylamine, makes only tetramethylphosphoroamidates and does not teach the use of phosphordiamidates as flame retardants, although disclosing certain compounds falling within the scope of formula (1) of this invention.

U.S. Pat. No. 3,328,494 discloses O-(2-naphthyl)phosphorothionates, which may be mono- or diamido substituted, having utility as herbicides. With regard to the present invention, the patent does not disclose a process suing an alkali metal hydroxide and, while disclosing certain N,N'-di-lower alkylamido compounds falling within the scope of formula (1) of this invention, does not distinguish between those compounds the the disclosed diamido compounds and does not teach the use of phosphorodiamidates as flame retardants.

U.S. Pat. No. 3,531,550 discloses certain phosphorus ester mono- and diamides having utility as functional fluids. With regard to the present invention, the patent does not use a process involving alkali metal hydroxide and, while disclosing certain compounds within the scope of formula (1) of this invention, does not teach the use of phosphorodiamidates as flame retardants.

U.S. Pat. No. 3,584,085 discloses the use of certain phosphoromonoamidates as flame retardants for polyurethanes. With regard to the present invention, the patent does not disclose the use of an alkali metal hydroxide and prepares hydroxyalkyl, halophenyl, hydrogen and alkyl-substituted amides which are not within the scope of formula (1) of this invention.

(c) Novel Phosphoroamidates

The following patents disclose phosphoroamidates which are relevant to the compounds of formula (2) of this invention:

U.S. Pat. No. 3,254,050
U.S. Pat. No. 3,335,129
W. German Pat. No. 2,104,569

U.S. Pat. No. 3,254,050 discloses certain bisphenol biphosphites as flame retardants for various resin systems. With regard to the present invention, the patent does not prepare amidates from bisphenol compounds as defined in formula (2) of the present invention.

U.S. Pat. No. 3,335,129 discloses certain phosphoromono- and diamidates having utility as flame retardants for various resin systems. With regard to the present invention, the patented compounds must contain free hydroxyl groups to provide a reactive site so the compounds may be reacted with the resin systems which they are intended to flame retard. In contrast thereto, the compounds of formula (2) of this invention contain no free hydroxyl groups.

W. German Pat. No. 2,104,569 discloses certain haloalkylamides as flame retardants for polyurethanes. The compounds of formulas (II) and (III) of the patent are distinguished from the compounds of formula (2) of this invention since the compounds of this invention are not haloalkylamide-substituted phosphorus compounds.

(d) Novel Polymer Compositions

The following patents disclose phosphoramidate/resin compositions which are relevant to the polymer compositions containing compounds as defined in formula (2):

U.S. Pat. No. 3,256,249
W. German Pat. No. 2,104,569

U.S. Pat. No. 3,256,249 is relevant to the polymer compositions of this invention which contain compounds of formula (2). The patent discloses hydroxylated phosphoromono- and diamides as flame retardants in various resin systems. In contrast thereto, the polymer compositions of this invention do not contain hydroxylated phosphoroamidate flame retardants.

W. German Pat. No. 2,104,569 discloses haloalkylamide-substituted phosphorus compounds as flame retardants for polyurethanes. With regard to the present invention, the compounds of formulas (II) and (III) of the patent are haloalkylamide-substituted compounds while those of formula (2) of this invention contain no haloalkylamide substituents.

SUMMARY OF THE INVENTION

It has been found that certain phosphoroamidates are useful as flame retardant additives and that such compounds may be prepared by the reaction of a phosphorus halidate with an amine in an organic diluent containing an aqueous solution of an alkali metal or ammonium hydroxide.

DESCRIPTION OF THE PREFERRED EMBODIMENT

The compounds of this invention are prepared by reaction of a hydroxyl-containing moiety with a phosphorus oxyhalide or phosphorus thiohalide to afford a phosphorohalidate which is then reacted with a secondary amine in an organic diluent containing an aqueous solution of an alkali metal hydroxide.

The compound of this invention are represented by the formulas

and

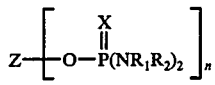

wherein

X represents oxygen or sulfur;

Z-represents the residue of a hydroxyl-containing moiety;

$R_1$ and $R_2$ in formula (1) individually represent alkyl, cycloalkyl or aryl, and may be the same or different and, together with their common nitrogen atom represent a 5 or 6 member ring containing oxygen, sulfur or nitrogen or combination thereof;

$NR_1R_2$ in formula (2) represents a 5 or 6-member ring containing oxygen, sulfur or nitrogen or combination thereof;

$n$ represents an integer having a value of 2 or greater and is equal to the number of hydroxyl groups on the original hydroxyl-containing moiety, the residue of which is herein-represented by Z.

It is understood that the acid and alkaline and ammonium salts of compounds of formulas (1) and (2) are within the scope of the invention, i.e., hydrochlorides, sulfates, toluenesulfonates and the like. Accordingly, reference hereinafter to a group of compounds or to a specific compound within a group is intended to include the acid and alkaline and ammonium slat thereof.

Generalized reaction schemes for preparing the compounds of formulas (1) and (2) of the invention are as follows:

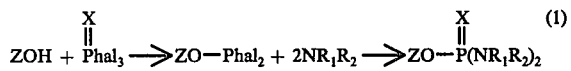

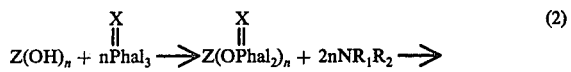

wherein X, Z, $R_1$, $R_2$ and $n$ are identified above.

Hydroxyl-containing compounds which are reacted with a phosphorus oxyhalide or thiohalide to obtain phosphorohalidates or thiophosphorohalides are represented by the formulas

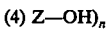

where $n$ represents an integer having a value of 2 or greater.

The particular hydroxyl-containing compound used is not critical, insofar as the preparation of the phosphorohalidate intermediate is concerned, since any hydroxyl-containing material which will react with a phosphorus oxyhalide or phosphorus thiohalide may be utilized. Additionally, the hydroxyl-containing compound may be the reaction product of a hydroxyl-containing compound and an alkylene oxide.

Illustrative examples of hydroxyl-containing compounds represented by ZOH and Z-(OH)$_n$ include substituted and nonsubstituted hydrocarbon chains which may be aliphatic or branched-chain, saturated or unsaturated, aromatic or mixed aliphatic/aromatic or cyclic in character, e.g., aliphatic and aromatic alcohols such as mono- and poly-hydroxy aliphatic or aromatic alcohols and phenols, carbohydrates and hydroxyl-containing higher polymers whether natural or synthetic in origin.

Exemplary aliphatic alcohols which are used include methanol, ethanol, propanol, isopropanol, butanol, isobutanol, nonanol, isononanol, decanol, octadecanol, allyl alcohol, phytol, ethylene glycol, farnesol, propylene glycol, trimethylene glycol, glycerol, β-chloroethanol, glycol methyl ether, glycol ethyl ether, citronellol, ethylene chlorohydrin, diethylene glycol, carbitol, 1,2-butanediol, 2,3-butanediol, pentamethylene glycol, geraniol, xanthyl alcohol, naphthyl alcohol, erythritol, arabitol, sorbitol, mixtures of $C_7$, $C_9$ and $C_{11}$ alcohols, and mixtures of $C_6$, $C_8$, $C_{10}$ and $C_{12}$ alcohols.

Cyclic alcohols include cyclopentanol, cyclohexanol, pentahydroxycyclohexane, terpineol, hexahydroxycyclohexane, cyclopropylcarbinol, borneol, cyclohexanediol, cyclohexanedimethanol.

Aromatic alcohols include trimellitic alcohol, benzyl alcohol, β-phenylethanol, β-phenoxyethanol, α-phenylethanol, phenylallyl alcohol, diphenylcarbinol, triphenylcarbinol, salicyl alcohol Phenols include phenol, bis(alkylidene)phenols such as 4,4'-isopropylidene diphenol, allylphenol, nitrosophenol, cresol, methyl phenol, ethyl phenol, thymol, carvacrol, p-α-propenylphenol, resorcinol, aminophenol, catechol, quinol, adrenaline, hexylresorcinol, hydroquinone, trihydroxybenzene, pyrogallol.

Carbohydrates include the aldotetroses, the aldopentoses, e.g., xylose, ribose, the aldohexoses, e.g., glucose, the disaccharides, e.g., sucrose, lactose, maltose, the trisaccharides, e.g., raffinose, sorbitol, rahmnose, fructose, glycosides, cellobiose, polysaccharides, e.g., starch, cellulose.

Higher polymer materials include the polyalkylene glycols, polyvinyl alcohol, hydrolyzed vinyl acetate/vinyl alcohol copolymers, phenolic resins.

Other hydroxyl-containing materials, such as dihydroxyacetone, glyceryl monostearate, glyceraldehyde, cellosolve acetate and hydroxyacetophenone may be used.

Primary or secondary alcohols or phenols are the preferred hydroxyl-containing material. Tertiary alcohols are unsuitable since reaction thereof with a phosphoryl halide affords an alkyl halide rather than a phosphorohalidate.

A preferred class of hydroxyl-containing compounds are represented by phenol, o, m, p-cresol, o-ethylphenol, o, m, p-isopropylphenol, p-tert-butylphenol, p-tert-amylphenol, nonylphenol, xylenol, o, m, p-chlorophenol, p-bromophenol, p-iodophenol, dichlorophenol, trichlorophenol, pentachlorophenol, p-cumylphenol, o-cyclohexylphenol, naphthol, methoxyphenol, ethoxyphenol, phenoxyphenol, p-nitrophenol, trifluoromethylphenol, allylphenol, benzylphenol, vanillin, 4-chloro-3,5-dimethylphenol, 4-chloro-1-naphthol, 2-chloro-4-nitrophenol, cyanophenol, di-tert-butylphenol, dimethoxyphenol, methylsalicylate, fluorophenol. Especially preferred of this group are phenol, cresol, cumylphenol, nonylphenol, chlorophenol, xylenol, tert-butylphenol, phenylphenol, isopropylphenol and mixtures thereof.

Another preferred class of hydroxyl-containing materials includes cyclohexanedimethanol, isopropylidene diphenol, hydroquinone, catechol and resorcinol.

It is essential that the alcohol, i.e. the original hydroxyl-containing moiety, contain no free-hydroxyl groups after the reaction with a phosphorus oxyhalide or phosphorus thiohalide, since a free-hydroxyl group would react with any remaining P-chlorine linkages, thus leaving no reactive site for the subsequent amidation.

Alkyl radicals represented by $R_1$ and $R_2$ in formulas (1) and (2) include methyl, ethyl, propyl, isopropyl, butyl, amyl, hexyl, heptyl, octyl, nonyl, decyl, octadecyl, benzyl, β-phenylethyl.

Aryl radicals represented by $R_1$ and $R_2$ in formulas (1) and (2) include phenyl, alkyl-substituted phenyl, e.g., methyl phenyl, diethyl phenyl, naphthyl, chlorophenyl.

Cycloalkyl radicals represented by $R_1$ and $R_2$ in formulas (1) and (2) include cyclohexyl, cyclopentyl, cyclobutyl.

Five and six-member rings, containing oxygen, sulfur, nitrogen and combinations thereof, represented by $R_1$ and $R_2$, together, in formulas (1) and (2) include thiazole, pyridine, pyrrole, isoxazole, oxazole, pyrazole, imidazole, thiazoline, thiazolidine, thiopyran, collidine, hexahydropyridine, piperidine, morpholine, condensed ring systems such as benzopyrrole, quinoline and carbazole.

The phosphorus halides and phosphorus thiohalides which are utilized herein include, for example, phosphorus oxytrichloride, phosphorus oxytribromide, phosphorus oxytrifluoride, phosphorus oxydichloride bromide, phosphorus oxydibromide chloride, phosphorus oxydifluoride chloride and the corresponding thiophosphorus analogs.

The phosphorohalidates, which are reacted with a secondary amine to obtain the compounds of this invention, are prepared as described above and by methods known in the art, are represented by the formulas

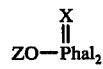  (5)

and

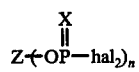  (6)

wherein hal represents halogen, e.g., chlorine, fluorine, bromine or iodine and Z, X and n are as defined in formulas (1) and (2).

Illustrative phosphorohalidates utilized to prepare the novel compounds of this invention include phenyl phosphorodichloridate, chlorophenyl phosphorodichloridate, chlorophenyl phosphorodibromidate, nitrophenyl phosphorodichloridate, cresyl phosphorodichloridate, methoxyphenyl phosphorodibromidate, nonylphenyl phosphorodichloridate, cumylphenyl phosphorodichloridate, biphenyl phosphorodichloridate, naphthyl phosphorodichloridate, isopropylphenyl phosphorodichloridate, tert-butylphenyl phosphorodichloridate, isodecylphenyl phosphorodichloridate, isodecyl phosphorodichloridate, isopropylidene di-p-phenylene bisphosphorodichloridate, isopropylidene di-p-phenyl phosphorodichloridate, cyclohexylenedimethylene bis phosphorodichloridate, dicresyl phosphorodichloridate, dixylyl phosphorodichloridate, n-propylene bis phosphorodichloridate, n-butylene bis phosphorodichloridate and the polyphosphorodichloridates of carbohydrates and other hydroxyl-containing polymeric materials.

The secondary amines utilized in accordance with this invention are characterized by the formula

  (7)

wherein $R_1$ and $R_2$ individually or together are as defined in formulas (1) and (2). Preferably, one of $R_1$ and $R_2$ is a methyl group.

Illustrative amines include the alkylamines, e.g., dimethylamine, methyl ethyl amine, methyl butyl amine, dibutyl amine, dioctyl amine, di-n-hexylamine, didecyl amine, di-n-octadecylamine, dibenzylamine, di-β-phenylethylamine; cycloalkyl amines, e.g., butylcyclohexyl amine, dicyclopentyl amine; and similar compounds.

The reaction of a slight excess of a polyfunctional amine with a phosphorohalidate affords polymeric compounds of this invention having the formula

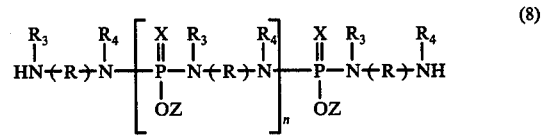  (8)

wherein
R represents an alkylene group of 1 to 50 carbon atoms or an arylene group;
$R_3$ and $R_4$ individually represent an alkyl group of 1 to 10 carbon atoms or, together with the nitrogen atom, a 5 or 6 member heterocyclic ring;
X represents oxygen or sulfur;
Z represents the residue of a hydroxyl-containing moiety; and
n represents an integer from 1 to 40.

Polyfunctional amines which are used to prepare the compounds of formula (8) are represented by the formula

  (9)

wherein R, $R_3$ and $R_4$ are defined in formula (8).

Illustrative amines corresponding to formula (9) include those compounds where R preferably represents an alkylene group of 1 to 10 carbon atoms and one of $R_3$ and $R_4$ is preferably methyl, e.g., bis(methylamino)methane, bis(methylamino)ethane, bis(methylamino)propane, bis(methylamino)butane, bis(ethylamino) octane, bis(methylamino)benzene and the like.

Preferred groups of compounds in accordance with this invention include compounds of the formulas

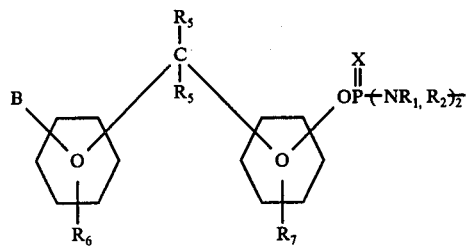 (10)

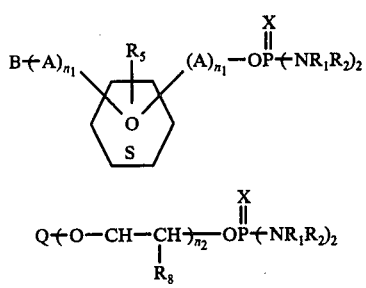 (11)

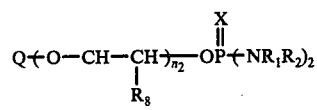 (12)

wherein
$R_1$ and $R_2$ individually represent an alkyl group of 1 to 10 carbon atoms or an aryl group or an alkyl-aryl group;
$R_1$ and $R_2$, each together with its attached nitrogen atom, represent a 5 or 6 member heterocyclic ring which may additionally contain oxygen, sulfur or nitrogen;
$R_5$ represents hydrogen, an alkyl group of 1 to 20 carbon atoms, an aryl group, an alkylaryl group or halogen;
$R_6$ and $R_7$ individually represent hydrogen, an alkyl group of 1 to 10 carbon atoms, an aryl group or an alkylaryl group;
$R_8$ represents hydrogen or an alkyl, cycloalkyl, alkaryl, aryl or aralkyl group;
X represents oxygen or sulfur;
A represents a methylene or phenylene group;
B represents hydrogen or

;

Q represents an alkyl group of 1 to 20 carbon atoms, an aryl group, an alkylaryl group, a carbonyl or sulfonyl group, an aliphatic or aromatic ester group or

;

$n_1$ represents an integer having a value of 0, or 1 to 6 when
A = methylene or 1 to 2 when A = phenylene; and
$n_2$ represents an integer having a value of 1 to 50.

Compounds of formula (10) are prepared, for example, by reaction of isopropylidene diphenol (e.g., bisphenol A) or phenylisopropylphenol with phosphorus oxychloride or phosphorus thiochloride and subsequent reaction of the phosphorodichloridate intermediate with a secondary amine described above.

Exemplary compounds represented by formula (10), where B = hydrogen, include:

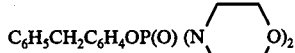

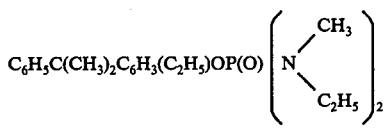

$C_6H_5CH_2C_6H_3(CH_3)OP(O)[N(C_3H_7)_2]_2$

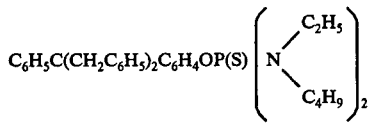

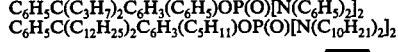

$C_6H_5C(C_3H_7)_2C_6H_3(C_6H_5)OP(O)[N(C_6H_5)_2]_2$
$C_6H_5C(C_{12}H_{25})_2C_6H_3(C_5H_{11})OP(O)[N(C_{10}H_{21})_2]_2$

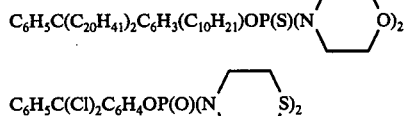

Exemplary compounds of formula (10), where B =

$-\overset{\overset{X}{\|}}{O}P(NR_1R_2)_2$, include:

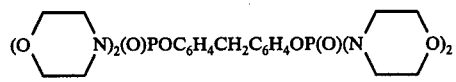

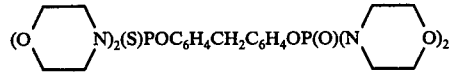

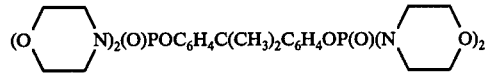

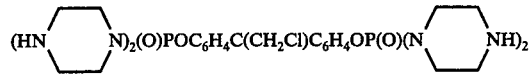

Compounds of formula (11) are prepared, for example, by reaction of benzyl alcohol, cyclohexanemethanol, phenylphenol, cyclohexanol, hydroxymethylphenol, hydroxycyclohexanemethanol, bis-hydroxy diphenyl, cyclohexanediol, cyclohexanedimethanol, bis(hydroxymethyl)benzene or other appropriate compounds with a phosphorus oxyhalide or phosphorus thiohalide and an amine, as described above with regard to formula (10).

Exemplary compounds represented by formula (11), where B = hydrogen, include:

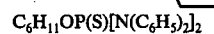

$C_6H_{11}OP(S)[N(C_6H_5)_2]_2$

-continued

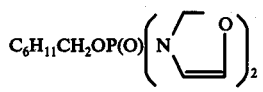

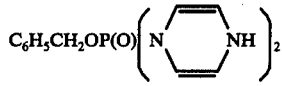

C$_6$H$_5$C$_6$H$_4$OP(O)[N(C$_4$H$_9$)$_2$]$_2$
C$_6$H$_{11}$OP(O)[N(CH$_3$)$_2$]$_2$

Exemplary compounds of formula (11), where

include:
[(H$_3$C)$_2$N]$_2$(O)POH$_2$CC$_6$H$_{10}$CH$_2$OP(O)[N(CH$_3$)$_2$]$_2$

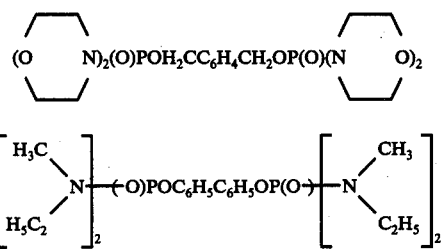

[(H$_3$C)$_2$N]$_2$(O(POC$_6$H$_{10}$OP(O)[N(CH$_3$)$_2$]$_2$

Compounds of formula (12) are prepared by reaction of a polyol (e.g., the reaction product of an alkylene oxide and a glycol) with a phosphorus oxyhalide or thiohalide and an amine ad described above.

Exemplary compounds represented by formula (12) include:

C$_{15}$H$_{31}$OC$_{15}$H$_{30}$OP(O)[N(CH$_3$)$_2$]$_2$

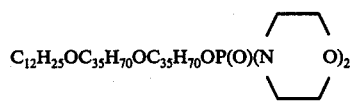

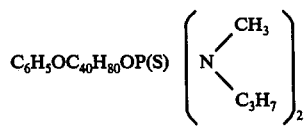

(CH$_3$)$_2$CHC$_6$H$_4$OC$_{50}$H$_{100}$OC$_{50}$H$_{100}$OP(O)[N(C$_2$H$_5$)$_2$]$_2$
H$_5$C$_2$OC(O)OC$_6$H$_{12}$OC$_6$H$_{12}$OP(O)[N(C$_5$H$_{11}$)$_2$]$_2$

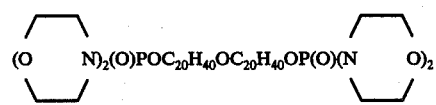

The proportion of phosphorodihalidate and amine which are reacted will vary, depending upon reaction conditions. Generally, however, sufficient amine is added to completely convert the phosphorodihalidate to the corresponding phosphorodiamidate, e.g., two moles or more of amine per mole of phosphorodihalidate.

The reaction of the phosphorodihalidate and amine may be conducted in an aqueous medium but is preferably conducted in an organic diluent containing an aqueous solution of an alkali metal or ammonium hydroxide so that the alkali metal hydroxide will scavenge liberated hydrogen chloride. Organic diluents which may be used include any of the conventional organic diluents such as chlorobenzene, tetrahydrofuran and the like.

The temperature of the phosphorohalidate/amine reaction may vary from about 0° to about 100° C., although the preferred temperature range is from about 10° to about 60° C. Higher temperatures may be used but reduce yield.

The following examples illustrate specific embodiments of the preparation of certain compounds of the invention and are not to be construed as limiting the scope thereof.

EXAMPLE 1

In a one-liter flask, fitted with mechanical stirrer, condenser and thermometer, are placed 228 g. (1.0 mole) of bisphenol A, 460 g. (3.0 moles) of phosphorus oxychloride, and 3.0 g. of pyridine. The solution is heated to reflux. At about 90° C., hydrogen chloride starts to evolve and is passed to a water scrubber. After 2½ hours, the temperature of the reaction mass stabilizes at 135° C. and no further hydrogen chloride is liberated. The excess phosphorus oxychloride is removed by vacuum distillating the mass at 100° C. to 40 mm of Hg. There is recovered 144 g. of phosphorus oxychloride. The residue is 459 g. of product (99% of theory) and is isopropylidene di-p-phenylene bis-phosphorodichloridate:

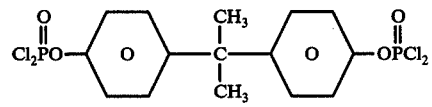

EXAMPLE 2

In a two liter flask, fitted with mechanical stirrer, dropping funnel, condenser and thermometer, are placed 800 g. of 25 percent dimethyl amine solution and 340 g. of 50 percent sodium hydroxide solution. The mixture is cooled during the addition to 15° C. by means of an ice water bath. By means of a dropping funnel, 461 g. (1.0 mole) of isopropylidene di-p-phenylene bis-phosphorodichloridate (prepared as described in Example 1) in 200 ml. of monochlorobenzene is added dropwise over a two hour period. The temperature is maintained at 15°±2° C. After the addition is complete, the mixture is stirred for one-half hour and then heated to 60° C. over a half hour period. Layers are separated and the organic layer is washed at 70° C. with 700 ml. of water for 20 minutes. The organic layer is then vacuum stripped to 135° C./40 mm. Hg and then steam sparged at 135° C./40 mm. Hg. for 30 minutes. The product is dehydrated and filtered. There is obtained 465 g. (94% of theory) of the product, which is isopropylidene di-p-phenylene bis(tetramethylphosphorodiamidate):

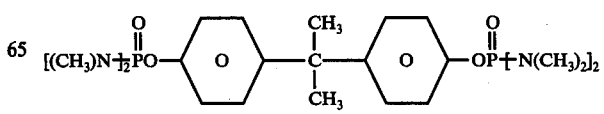

EXAMPLE 3

Morpholine (400 gms.) is dissolved in 600 ml. water, cooled to 15° C. in a 2 liter, 3-necked flask cooled by a water bath. A fifty percent solution of sodium hydroxide (340 gms.) is added and then, using a dropping funnel, isopropylidene di-p-phenylene bis phosphorodichloridate (461 gms.) in monochlorobenzene (200 ml.) is added over a two-hour period maintaining the temperature at 15°±2° C. After addition, the mixture is stirred at 15° C. for one-half hour and then heated to 60° C. over one-half hour. The mixture is placed in a two liter separatory funnel and the salt layer is discarded. The organic layer is washed with 700 ml. water at 60°–65° C. for 2 minutes. The water layer is discarded and the organic layer is washed with 10 gms. sodium hydroxide in 700 ml. water at 70°–75° C. for 20 minutes, stripped and steamed at 135° C./40 mm. Hg. for one-half hour. There is obtained a 90 percent yield of product, isopropylidene di-p-phenylene bis(dimorpholinophosphorodiamidate):

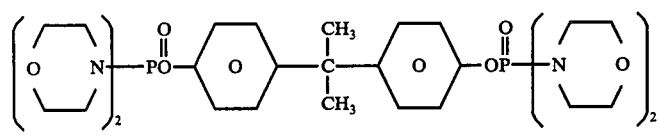

Substituting other amines in place of morpholine in the above procedure affords the following compounds:

| Amine | Compound |
|---|---|
| HN⟨N⟩ | (HN⟨N⟩)₂(O)POC₆H₄C(CH₃)₂C₆H₄OP(O)(N⟨NH⟩)₂ |
| HN⟨S⟩ | (⟨S⟩N)₂(O)POH₄C₆C(CH₃)₂C₆H₄OP(O)(N⟨S⟩)₂ |
| HN⟨O⟩ (unsaturated) | (⟨O⟩N)₂(O)POC₆H₄C(CH₃)₂C₆H₄OP(O)(N⟨O⟩)₂ |

EXAMPLE 4

In a one liter flask, fitted with reflux condenser thermometer and mechanical stirrer, are placed cumylphenol (424 gms.), phosphorus oxychloride (460 gms.) and pyridine (3.0 gms.). The mixture is heated to reflux which starts at 95° C. with evolution of hydrogen chloride. Over a period of three hours the temperature slowly rises to 145° C. and is maintained at that temperature for an additional one-half hour. The mixture is vacuum stripped to recover phosphorus oxychloride. The residue is diluted with monochlorobenzene (200 ml.) and added to a previously prepared solution of dimethylamine (800 gms. — 25 percent in water) and sodium hydroxide (350 gms. — 50 percent in water). The mixture is cooled to 15°–20° C. during the addition over one and one-half hours. The mixture is then heated to 70° C. and the layers are separated. The organic layer is washed with water at 70° C., dehydrated, steamed and filtered.

The product (628 gms. — 91 percent yield) is cumylphenyl tetramethylphosphorodiamidate:

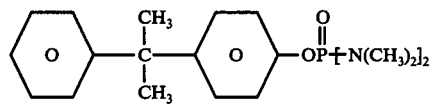

EXAMPLE 5

In a one liter flask, fitted with reflux condenser, mechanical stirrer and thermometer, are placed nonylphenol (440 gms.), phosphorus oxychloride (460 gms.) and pyridine (3.0 gms.). The procedure of Example 4 is then followed and the mixture residue is diluted with monochlorobenzene (200 ml.) and added to a morpholine (400 gms.)/caustic (350 gms.) solution. A ninety percent yield (787 gms.) of nonylphenyl dimorpholinophosphorodiamidate is obtained:

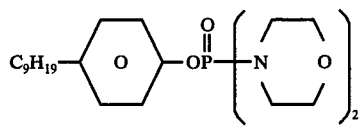

Repeating the above procedure with substitution of 800 gms. dimethylamine of 25 percent solution for 400 gms. morpholine affords a ninety percent yield (633 gms.) of nonylphenyl tetramethylphosphorodiamidate:

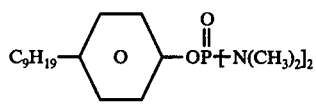

EXAMPLE 6

In a one liter flask, equipped as in Example 4, are placed cyclohexanedimethanol 1,4 (3 moles), phosphorus oxychloride (3 moles) and pyridine (3 grams). The procedure of Example 4 is then followed and the reaction mixture is diluted with chlorobenzene and added to 4 moles of dimethylamine in caustic. The product is cyclohexylenedimethylene bis(tetramethylphosphorodiamidate), $[(H_3C)_2N]_2(O)POCH_2C_6H_{10}CH_2OP(O)[N(CH_3)_2]_2$.

Dimethylamine may be replaced by other secondary amines to afford desired analogous phosphoroamidates.

EXAMPLE 7

To a 50 gal. steel-jacketed vessel, equipped with agitator and thermowell, there is charged phosphorus oxychloride and diethylene glycol in a 2:1 molar ratio. After reaction at 15° C. for two hours and 30° C. for one hour, there is added a 25 percent solution of dimethylamine in caustic in a ratio of four moles of dimethylamine to each mole of diethylene glycol bis phosphorodichloridate intermediate. The temperature is lowered to 15° C. and held for 30 minutes. An 88 percent yield of product is afforded, which is diethylene glycol bis(tetramethylphosphorodiamidate), $[(H_3C)_2N]_2(O)POCH_2CH_2OCH_2CH_2OP(O)[N(CH_3)_2]_2$.

The compounds of the present invention are useful as flame retardants for a wide variety of natural and synthetic polymer materials. The compounds may be used in concentrations of from about 0.1 percent by weight of polymer up to about 50 weight percent or more depending on the particular use for which the polymer material is intended.

Synthetic polymer materials, i.e., those high molecular weight organic materials which are not found in nature, with which the compounds of the invention are advantageously employed may be either linear or crosslinked polymers and may be in the form of sheets, coatings, foams and the like. They may be either those which are produced by addition or condensation polymerization.

An important class of polymers which are beneficially flame retarded with the compounds of the invention are those obtained from a polymerizable monomer compound having ethylenic unsaturation. A particularly preferred class of polymers which are flame retarded consist of the polymerized vinyl and vinylidene compounds, i.e., those having the $CH_2 = C <$ radical. Compounds having such a radical are, for example, the solid polymeric alkenes, such as polyethylene, polypropylene, polyisobutylene or ethylene/propylene copolymers; polymerized acrylyl and alkacrylyl compounds such as acrylic, fluoroacrylic and methacrylic acids, anhydrides, esters, nitriles and amides, for example, acrylonitrile, ethyl or butyl acrylate, methyl or ethyl methacrylate, methoxymethyl or 2-(2-butoxyethoxy)ethyl methacrylate, 2-(cyanoethoxy)ethyl 3-(3-cyanopropoxy)propyl acrylate or methacrylate, 2(diethylamino)ethyl or 2-chloroethyl acrylate or methacrylate, acrylic anhydride or methacrylic anhydride; methacrylamide or chloroacrylamide; ethyl or butyl chloroacrylate; the olefinic aldehydes such as acrolein, methacrolein and their acetals; the vinyl and vinylidene halides such as vinyl chloride, vinyl fluoride, vinylidene fluoride and 1-chloro-1-fluoroethylene; polyvinyl alcohol; the vinyl carboxylates such as vinyl acetate, vinyl chloroacetate, vinyl propionate, and vinyl 2-ethyl-hexanoate; the N-vinyl imides such as N-vinyl phthalimide and N-vinylsuccinamide; the N-vinyl lactams such as N-vinyl caprolactam and N-vinyl butyrolactam; vinyl aromatic hydrocarbon compounds such as styrene, alpha-methylstyrene, 2,4-dichlorostyrene, alpha- or beta-vinylnaphthalene, divinyl benzene and vinyl fluorene; the vinyl ethers such as ethyl vinyl ether or isobutyl vinyl ether; vinyl-substituted heterocyclic compounds such as vinyl pyridine, vinyl pyrrolidone, vinylfuran or vinylthiophene; the vinyl or vinylidene ketones such as methyl vinyl ketone or isopropenyl ethyl ketone; vinylidene cyanide. Homopolymers of the above compounds or copolymers and terpolymers thereof are beneficially flame retarded by the compounds of the present invention. Examples of such copolymers or terpolymers are those obtained by polymerization of the following monomer mixtures; vinyl chloride/vinyl acetate, ethylene/vinyl chloride/vinyl acetate, acrylonitrile/vinyl pyridine, styrenemethyl/methacrylate, styrene/N-vinyl pyrrolidone, cyclohexyl methacrylate/vinyl chloroacetate, acrylonitrile/vinylidene cyanide, methyl methacrylate/vinyl acetate, ethyl acrylate/methacrylamide/ethyl chloroacrylate, vinyl chloride/vinylidene chloride/vinyl acetate.

Other polymers of compounds having the ethylenic group, $>C=C<$, are homopolymers, copolymers and terpolymers of the alpha-, beta-olefinic dicarboxylic acids and derivatives thereof such as the anhydrides, esters, amides, nitriles and imides, for example, methyl, butyl, 2-ethylhexyl or dodecyl fumarate or maleate; maleic, chloromaleic, citraconic or itaconic anhydride; fumaronitrile, dichlorofumaronitrile or citracononitrile; fumaramide, maleamide or N-phenyl maleamide. Examples of particularly useful polymers and terpolymers prepared from the alpha-, beta-olefinic dicarboxylic compounds are the copolymers of maleic anhydride and a vinyl compound such as ethylene, propylene, isobutylene, styrene, alpha methylstyrene, vinyl acetate, vinyl propionate, methyl isopropenyl ketone, isobutyl vinyl ether, the copolymers of dialkyl fumarate such as ethyl or butyl fumarate and vinyl compounds such as styrene, vinyl acetate, vinylidene chloride, ethyl methacrylate, acrylonitrile and the like.

The compounds of the invention act as flame retardants for the polymers and copolymers of unsaturated, cyclic esters of carbonic acid, for example, homopolymeric vinylene carbonate or the copolymers of vinylene carbonate with ethylenic compounds such as ethylene, vinyl chloride, vinyl acetate, 1,3-butadiene, acrylonitrile, methacrylonitrile, or the esters of methacrylic or acrylic acid.

Readily flame retarded by the compounds of the invention are also the polyarylcarbonate polymers such as the linear polyarylcarbonates formed from diphenols or dihydroxy aromatic compounds including single and fused-ring nucleii with two hydroxy groups as well as monohydroxy-substituted aromatic residues joined in pairs by various connecting linkages. Examples of the foregoing include dihydroxy benzenes, naphthalenes and the like, the dihydroxydiphenyl ethers, sulfones, alkanes, ketones and the like.

The compounds of the invention also act as flame retardants for polymers, copolymers or terpolymers of polymerizable compounds having a plurality of double bonds, for example, rubbery, conjugated diene polymerizates such as homopolymerized 3-butadiene, 2-chlorobutadiene or isoprene and linear copolymers or terpolymers such as butadiene/acrylonitrile, isobutylene/butadiene, butadiene/styrene; esters of saturated di- or poly-hydroxy compounds with olefinic carboxylic acids such as ethylene glycol dimethacrylate, triethylene glycol dicrotonate or glyceryl triacrylate; esters of olefinic alcohols with dicarboxylic acids or with olefinic monocarboxylic acids such as diallyl adipate, divinyl succinate, diallyl fumarate, allyl methacrylate or crotyl acrylate and other diethylenically unsaturated compounds such as diallyl carbonate, divinyl ether or divinylbenzene, as well as the crosslinked polymeric materials such as methyl methacrylate/diallyl methacrylate copolymer or butadiene/styrene/divinyl benzene terpolymer.

The cellulose derivatives are flame retarded by the compounds of the present invention. For example, cellulose esters such as cellulose acetate, cellulose triacetate or cellulose butyrate, the cellulose ethers such as methyl or ethyl cellulose, cellulose nitrate, carboxymethyl cellulose, cellophane, rayon, regenerated rayon the the like may be flame retarded.

The compounds of the present invention are well suited for flame retarding liquid resin compositions of the polyester type, for example, the linear polyesters which are obtained by the reaction of one or more polyhydric alcohols with one or more alpha, beta-unsaturated polycarboxylic acids alone or in combination with one or more saturated polycarboxylic acid compounds, or the crosslinked polyester resins which are obtained by reacting a linear polyester with a compound containing a $CH_2 = C$ group.

The compounds of the present invention are compatible flame retardants for epoxy resins. Such resins are condensation products formed by the reaction of a polyhydroxy compound and epichlorohydrin, which condensation products are subsequently cured by the addition of crosslinking agents. The hydroxy compounds may be, for example, ethylene glycol, 4,4'-isopropylidenediphenol and similar materials. The crosslinking agent employed in the curing step may be a dicarboxylic compound such as phthalic anhydride or adipic acid, but is more generally a polyamine such as ethylene diamine, paraphenylamine diamine or diethylene triamine.

Polyurethanes are a class of polymer materials which are flame retarded by the compounds of the present invention. The polyurethanes, like the above-mentioned polyesters, are materials which are employed in structural applications, for example, as insulating foams, in the manufacture of textile fibers, as resin bases in the manufacture of curable coating compositions and as impregnating adhesives in the fabrication of laminates of wood and other fibrous materials. Essentially, the polyurethanes are condensation products of a diisocyanate and a compound having a molecular weight of at least 500 and preferably about 1500–5000 and at least two reactive hydrogen ions. The useful active-hydrogen containing compounds may be polyesters prepared from polycarboxylic acids and polyhydric alcohols, polyhydric polyalkylene ethers having at least two hydroxy groups, polythioether glycols, polyesteramides and similar materials.

The polyesters or polyester amides used for the production of the polyurethane may be branched and/or linear, for example, the esters of adipic, sebasic, 6-aminocaproic, phthalic, isophthalic, terephthalic, oxalic, malonic, succinic, maleic, cyclohexane-1,2-dicarboxylic, cyclohexane-1,4-dicarboxylic, polyacrylic, naphthalene-1,2-dicarboxylic, fumaric or itaconic acids with polyalcohols such as ethylene glycol, diethylene glycol, pentaglycol, glycerol, sorbitol, triethanolamine and/or amino alcohols such as ethanolamine, 3-aminopropanol, and with mixtures of the above polyalcohols and amines.

The alkylene glycols and polyoxyalkylene or polythioalkylene glycols used in the production of polyurethanes may be ethylene glycol, propylene glycol, butylene glycol, diethylene glycol, triethylene glycol, polythioethylene glycol, dipropylene glycol and the like.

Generally, any of the polyesters, polyisocyanate-modified polyesters, polyester amides, polyisocyanate-modified polyester-amides, alkylene glycols, polyisocyanate-modified alkylene glycols, polyoxyalkylene glycols and polyisocyanate-modified polyoxyalkylene glycols having three reactive hydrogen atoms, three reactive carboxylic and/or especially hydroxyl groups may be employed in the production of polyurethanes. Moreover, any organic compound containing at least two radicals selected from the group consisting of hydroxy and carboxy groups may be employed.

The organic polyisocyanates useful for the production of polyurethanes include ethylene diisocyanate, ethylidene diisocyanate, propylene-1,2-diisocyanate, m-phenylene diisocyanate, 2,4-tolylene diisocyanate, triphenylmethane triisocyanate, or polyisocyanates in blocked or inactive form such as the bisphenyl carbamates of tolylene diisocyanate and the like.

Phenolic resins are flame retarded by the compounds of the present invention, which compounds may be incorporated into the phenolic resin either by milling and molding applications or by addition to film-forming or impregnating and bonding solutions prior to casting. Phenolic resins with which the present compounds are employed are, for example, the phenol-aldehyde resins prepared from phenols such as phenol, cresol, xylinol, resorcinol, 4-butylphenol, cumylphenol, 4-phenylphenol, nonylphenol, and aldehydes such as formaldehyde, acetaldehyde or butyraldehyde in the presence of either acetic or basic catalysts, depending upon whether the resin is intended for use as a molding or extruding resin or as the resin base in coating and impregnating compositions.

Aminoplasts are another group of aldehyde resins which are flame retarded by the compounds of the invention. Examples of aminoplasts are the heat-convertible condensation products of an aldehyde with urea, thiourea, guanidine, cyanamide, dicyandiamide, alkyl or aryl guanamines and the triazines such as melamine, 2-fluoro-4,6-diamino-1,3,5-triazine and the like. When the aminoplasts are to be used as impregnating agents, bonding adhesives, coatings and in casting the films, the compounds of the present invention are incorporated into solutions or suspensions in which the aminoplast is carried. The resulting mixtures give strong, fire-retardant laminates when sheets of paper, glass, cloth or fabric are impregnated therewith and cured.

Another class of compounds which are flame retarded by the compounds of the present invention are the nylons, for example, the superpolyamides which are generally obtained by the condensation of a diamine, for example, hexamethylene diamine with a dicarboxylic acid, for example, adipic acid.

Other polyamides which are flame retarded in accordance with the present invention are the polypeptides which may be prepared, for example, by reaction of N-carbobenzyl oxyglycine with glycine or mixture of glycine and lysine or an N-carboxy amino acid anhydride such as N-carboxy-DL-phenylalanine anhydride, piperidone, 2-oxyhexamethyleneimine and other cyclic amides. The compounds of the present invention can be incorporated into molding or extruding compositions for a flame retardant effect.

The compounds of the present invention are also useful as flame retardants for linear polymers obtained by the self-condensation of bifunctional compounds, for example, the polyethers which are derived by the self-condensation of dihydric alcohols such as ethylene glycol, propylene glycol or hexamethylene glycol; the polyesters which are obtained by the self-condensation of hydroxy acids such as lactic acid or 4-hydroxybutyric acid; the polyamides which are prepared by the self-condensation of aminocarboxylic acids such as 4-aminobutyric acid; the polyanhydrides which are formed by the self-condensation of dicarboxylic acids such as sebasic or adipic acid.

The preferred synthetic polymer materials which are flame retarded by the compounds of the present invention are the vinyl halide polymers in the form of milled products, plastisols and foams, rigid and flexible polyurethane coating and foams, epoxy resins, ABS and GRS rubbers, aminoplasts and phenolics. The vinyl halide polymers can be simple, mixed homopolymers of vinyl chloride or vinylidene chloride, such as polyvinyl chloride or polyvinylidene chloride, or copolymers or terpolymers in which the essential polymeric structure of polyvinyl chloride is interspersed at intervals with residues of other ethylenically unsaturated compounds copolymerizable therewith. The essential properties of the polymeric structure of polyvinyl chloride is retained if not more than about 40 percent of a comonomer is copolymerized therewith. Especially preferred copolymers include ethylene/vinyl chloride and vinyl chloride/acrylonitrile copolymers. Especially preferred terpolymers include ethylene/vinyl chloride/acrylonitrile, ethylene/vinyl chloride/acrylic acid and ethylene/vinyl chloride/acrylamide terpolymers.

Natural polymeric materials which may be flame retarded by the compounds of the present invention include natural rubber, cellulose esters, for example, cellulose acetate and cellulose nitrate, ethyl cellulose, cork and wood flour products and similar cellulosic materials.

The polymer formulations which are flame retarded in accordance with the present invention, whether in sheet or film form or of foam or molded structure, may contain various conventional additives such as fillers, extenders crosslinking agents and colorants. Minor amounts of stabilizers, for example, are usually incorporated to reduce the effects of heat and light.

When foamable compositions are used, the composition may be a self-blowing polymer or the polymer may be blown by chemical or mechanical means or by the use of compressed gas. Fillers which are frequently employed to lower the cost of the finished material and to modify its properies include calcium carbonate and magnesium silicate. When fillers are employed, they are generally present in an amount of up to about 150 parts by weight of filler per 100 parts by weight of polymer formulation.

Where a colored or tinted composition is desired, colorants or color-pigments are incorporated in amounts of from about one to about five parts by weight to 100 parts by weight of polymer.

Surfactants such as silicones are normally added to foam formulations which are mechanically frothed. The surfactants reduced the surface tension of the foam and thereby increase the air or gas entrapment characteristics of the foam.

Additionally, glass-forming inorganic materials such as zinc borate, zinc oxide, lead oxide, lead silicate and silicon dioxide may be added to decrease the flame and smoke generating characteristics of the polymer. The flame retardant compounds of the present invention are extremely advantageous because of the following combination of properties: (1) The compounds are stable at temperatures somewhat in excess of 350° C. and can therefore be processed on standard machinery, such as milling machines, without degradation or color loss. (2) The compounds contain little or no chlorine and therefore contribute little or no hydrogen chloride gas during exposure to flames. (3) The compounds are amenable to formulation with a less stable acid generator and therefore can be made todegrade at lower temperatures if necessary. (4) The compounds are excellent acid scavengers, thereby decreasing the amount of acid radicals evolved by burning materials. (5) The compounds have high solubility and compatibility with a wide variety of synthetic and natural polymer materials.

The following examples will serve to illustrate the utility of the flame retardant compounds of the present invention in various polymer substances. The "oxygen index" referred to is that data obtained in accordance with ASTM D2863-70 and is defined as the minimum concentration of oxygen, expressed as volume percent, in a mixture of oxygen and nitrogen that will just support combustion of the material under the conditions of the test procedure.

EXAMPLE 8

In this example, the compound of Example 2 is compared with a commercially available flame retardant (ethylene glycol polyphosphate) in a commercial epoxy resin ("EPI-REZ", a trade mark of Celanese Chemical Company for their epoxy resin). The comparative properties of the resin containing 5 and 10 phr (parts per hundred resin) of the flame retardants are shown in the table below.

TABLE I

| Flame Retardant | phr | Volatility % Loss | Tensile psi | Oxygen Index % Oxygen |
|---|---|---|---|---|
| ethylene glycol polyphosphate | 5 | +0.59 | 2650 | 21.2 |
| ethylene glycol polyphosphate | 10 | +0.03 | 1920 | 21.2 |
| Example 2 Compound | 5 | +0.01 | 3200 | 22.0 |
| Example 2 Compound | 10 | +0.02 | 2880 | 24.0 |

EXAMPLE 9

In this example, the compound of Example 2 is formulated with a polymethyl methacrylate resin and compared with a control sample containing no flame retardant material. The control sample of polymethyl methacrylate had an oxygen index of 16.8 whereas the sample of polymethyl methacrylate containing 10 phr of the compound of Example 2 of the present invention had an oxygen index of 18.4 and a polymethyl methacrylate sample containing 30 phr of the compound of Example 2 had an oxygen index of 21.9.

EXAMPLE 10

The compound of Example 2 is compared with ethylene glycol polyphosphate in a melamine/formaldehyde resin at a level of 5 phr. The resin characteristics are shown in the table below:

TABLE II

| Flame Retardant | phr | Volatility %Loss | Oxygen Index - %Oxygen |
|---|---|---|---|
| Ethylene glycol polyphosphate | 5 | 12.0 | 48.2 |
| Compound of Example 2 | 5 | 10 | 49.3 |

EXAMPLE 11

The compound of Example 2 was formulated at 10 and 30 phr with a thermoplastic polyurethane resin. The material was rolled-milled for five minutes at 330° F., and molded at 320° F. for five minutes at 1000 psi. The characteristics of the resin are set forth in the following table.

TABLE III

| Flame Retardant | phr | Oxygen Index % Oxygen |
|---|---|---|
| Control | — | 20.6 |
| Compound of Example 2 | 10 | 22.4 |
| Compound of Example 2 | 30 | 27.6 |

Comparable flame retardancy is attained by substituting the compounds of Examples 3, 4, 5, 6 and 7 for the compound of Example 2 in the formulations of Examples 7 through 11.

While the invention has been described hereinabove with regard to certain illustrative, specific embodiments, it is not so limited since many modifications and variations are possible in the light of the above teachings. It is understood, therefore, that the invention may be practiced otherwise than as specifically described without departing from the spirit and scope of the invention.

The embodiments of the invention in which an exclusive property or privilege is claimed are defined as follows:

1. A compound of the formula

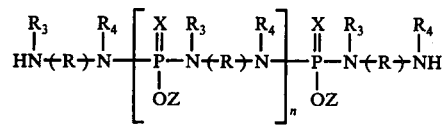

wherein

R represents an alkylene group of 1 to 50 carbon atoms or an arylene group;

$R_3$ and $R_4$ individually represent an alkyl group of 1 to 10 carbon atoms;

X represents oxygen or sulfur;

Z represents the residue of a hydroxyl-containing moiety which will react with a phosphorus oxyhalide or phosphorus thiohalide, said residue containing no free hydroxyl groups; and n represents an integer of from 1 to 40.

2. Compound of claim 1 wherein R represents an alkylene group of 1 to 10 carbon atoms, $R_3$ and $R_4$ represent methyl and X represents oxygen.

* * * * *

UNITED STATES PATENT AND TRADEMARK OFFICE
CERTIFICATE OF CORRECTION

PATENT NO. : 4,086,302
DATED : April 25, 1978
INVENTOR(S) : Albert W. Morgan, Ignatius Schumacher and William Vanderlinde It is certified that error appears in the above-identified patent and that said Letters Patent are hereby corrected as shown below:

Front page, in the abstract, in front of the two (2) formulae, there should be inserted, respectively, -- (1) -- and -- (2) --.

Column 3, line 18, "compound" should be corrected to read -- compounds --.

Column 3, line 23, before the formula should be inserted -- (1) --.

Column 3, line 26, before the formula should be inserted -- (2) --.

Column 4, line 3, before the formula should be inserted -- (3) --.

Column 7, in formula (10), "$(NR_1,R_2)_2$" should be corrected to read -- $(NR_1R_2)_2$ --.

Column 9, line 35, "ad" should be corrected to read -- as --.

UNITED STATES PATENT AND TRADEMARK OFFICE
CERTIFICATE OF CORRECTION

PATENT NO. : 4,086,302

DATED : April 25, 1978

INVENTOR(S) : Albert W. Morgan, Ignatius Schumacher and William Vanderlinde

It is certified that error appears in the above-identified patent and that said Letters Patent are hereby corrected as shown below:

Column 13, line 6, in the formula, "$POCHl_2$" should be corrected to read -- $POCH_2$ --.

Signed and Sealed this

Third Day of October 1978

[SEAL]

Attest:

RUTH C. MASON
*Attesting Officer*

DONALD W. BANNER
*Commissioner of Patents and Trademarks*